United States Patent [19]
Rones et al.

[11] Patent Number: 5,152,981
[45] Date of Patent: Oct. 6, 1992

[54] NEWCASTLE DISEASE VIRUS VACCINE AND METHOD FOR THE APPLICATION THEREOF

[75] Inventors: Zichria Z. Rones; Reuven Levy, both of Jerusalem, Israel

[73] Assignee: Yissum Research Development Company of the Hebrew University of Jerusalem, Jerusalem, Israel

[21] Appl. No.: 193,497

[22] Filed: May 12, 1988

[30] Foreign Application Priority Data

May 19, 1987 [IL] Israel ................................ 82586
Jan. 29, 1988 [IL] Israel ................................ 85266

[51] Int. Cl.$^5$ ...................... A61K 39/12; A61K 39/00
[52] U.S. Cl. ........................................... 424/89; 424/88
[58] Field of Search ..................... 424/89, 88

[56] References Cited

U.S. PATENT DOCUMENTS 4,053,583  10/1977  Gits et al. ............................... 424/90
4,279,893   7/1981  Kreimer et al. ......................... 424/89

FOREIGN PATENT DOCUMENTS 8600811  10/1986  PCT Int'l Appl. .

OTHER PUBLICATIONS

Herbert, *The Lancet*, vol. II, p. 771, Oct. 16, 1965.
Ernowati et al., "New castle disease vaccination in Malaysia & Application of oil emulsion vaccine" The Veterinary Record, vol. 115, No. 14 pp. 352-354, Oct. 1984.
Commonwealth Agricultural Bureau, ref. 83411929.
Biological Abstracts, vol. 66, No. 1, 1978, p. 246, ref. 2572.
Commonwealth Agricultural Bureau, ref. 87348881.
Commonwealth Agricultural Bureau, ref. 78534197.

*Primary Examiner*—Johnnie R. Brown
*Assistant Examiner*—Abdel A. Mohamed
*Attorney, Agent, or Firm*—Bachman & LaPointe

[57] ABSTRACT

The invention provides a vaccine against Newcastle Disease comprising a live immunogenic lentogenic or mesogenic strain of Newcastle Disease virus in combination with a liquid containing a mineral or vegetable oil adjuvant carrier together with instruction for the administering thereof to the respiratory tract of poults or chicks. The invention also provides a method for vaccinating chicks and poults against Newcastle Disease, comprising administering to the respiratory tract of said chicks and poults, at any time immediately after hatching and thereafter, a live immunogenic lentogenic or mesogenic strain of Newcastle Disease virus (NDV) in combination with a liquid containing a mineral or vegetable oil adjuvant carrier, to produce local antibodies in the respiratory tract thereof and confer an extended immunity against Newcastle Disease.

24 Claims, No Drawings

NEWCASTLE DISEASE VIRUS VACCINE AND METHOD FOR THE APPLICATION THEREOF

The present invention relates to vaccines and to a new approach for their application. More particularly, the present invention is directed to a new method of vaccinating chicks and poults at any time after hatching against Newcastle Disease Virus (NDV).

ND is a Paramyxovirus which belongs to the group of Myxoviruses. It has a major economic importance in the poultry industry, as losses from NDV may amount to many millions of U.S. dollars per year. Epidemics of ND are known since 1926. The disease is contagious and is easily transmitted from infected fowl and also from offal or garbage of infected, even frozen, poultry meat, due to the stability of the virus at different temperatures. The virus mainly attacks chickens and turkeys, as well as many other species of birds such as ducks, geese, pigeons, quails and pet birds.

Infection ranges from heavy mortality to asymptomatic infection. The most common signs of ND in chickens are respiratory in nature, gasping, coughs, etc. Nervous signs include partial or complete paralysis of the extremities, and muscular tremor usually follow or accompany the respiratory signs. Nervous manifestations can also occur on their own.

In younger birds, mortality may range from a low percentage to a hundred percent. The disease usually appears suddenly and spreads quickly through fully susceptible flocks. In laying flocks, respiratory symptoms are manifested and egg production might drop to a low level or zero. Mortality in laying flocks varies from zero to 100% depending on the viral strain.

All strains of ND are morphologically, structurally and serologically indistinguishable. However, large differences exist in the virulence of different strains for chickens, eggs and tissue culture systems. These differences are expressed in the classification of the different strains as velogenic, mesogenic and lentogenic strains. Lentogenic strains—apathogenic—are used in the preparations of most live vaccines. Mesogenic—intermediate in pathogenicity—are used as vaccinal strains for boosting the immunity of older fowls, e.g. in such commercially available mesogenic strains as Komarov (Haifa) and Roakin. Velogenic strains are highly pathogenic and are used for challenge, i.e., for testing immunity and mortality. The virus is pleomorphic, with a diameter ranging from 100-250 nm. The virion consists of coiled nucleocapsid containing RNA single stranded and 6-10 structural polypeptides (20,000-180,000 M.W.). The nucleocapsides are enveloped within protein and lipid envelopes. In the lipid layer two glycoproteins are inserted, the HN and F, which are responsible for the hemagglutination of erythrocytes and neuraminadase activity (HN) and fusion and hemolysis activities (F). These surface glycoproteins play a major role in the antigenicity and immunogenicity of the virus. The state of cleavage of these surface glycoproteins, F and HN is responsible for the virulence of the strains. Elicitation of antibodies versus these glycoproteins by vaccination is the manner in which fowl are protected.

Despite the widefelt need therefor, an effective vaccine against ND is still lacking at present. Both live and inactivated vaccines are used, each having its advantages and disadvantages. Lentogenic, and mesogenic strains are used for live vaccines and velogenic strains are being used for inactivated vaccines in different methods according to the age of the flocks to be immunized.

Immunization of young chicks, with the lentogenic strains, has heretofore been inefficient and of short duration. The use of mesogenic strains, used heretofore only in the vaccination of older chickens is limited because of their reactogenicity and possible subsequent risks, particularly by transmission to non-immunized chicks.

Inactivated oil-adjuvanted vaccine, which was introduced several years ago, is a highly popular vaccine today based on the use of killed virus (inactivated), as opposed to live virus vaccine, and is administered intramuscularly or subcutaneously. However, this type of vaccine solves only part of the problems concerning ND control. A major obstacle on the road to immunization of chicks with inactivated oil adjuvant vaccine is the presence of maternal antibodies. Maternal antibodies interfere with the adequate establishment of active immunity, unless a very large concentration of antigen is used. In order to overcome this obstacle, a combined immunization schedule, for one day old chicks simultaneously employing an aerosol of an aqueous solution containing lentogenic live vaccine and systemic (parenteral) injection of inactivated oil adjuvant vaccine, was introduced.

Schedules of fowl vaccination with available vaccines are cumbersome. As a routine, several repeated doses over a short period of time are required and these do not always give satisfactory results. Since the inactive vaccine is costly it was felt that a new approach to vaccination should be taken to combat ND.

An ideal vaccine is one that would confer immunity to a young chick, preferably from close to the time of hatching.

According to the present invention there is now provided a vaccine against Newcastle Disease comprising a live immunogenic lentogenic or mesogenic strain of Newcaste Disease virus in combination with a liquid containing a mineral or vegetable oil adjuvant carrier together with instruction for the administering thereof to the respiratory tract of poults or chicks.

It has been suprisingly found that the presence of mineral or vegetable oil results in augmentation of virus antigenicity, enhancement of cells of the immune system and retention of antigens in the respiratory tract both with regard to the lentogenic and with regard to the mesogenic strains of NDV when used according to the methods of the present invention.

The oil can be used as the sole adjuvant carrier or can be intermixed with aqueous distilled water, Phosphate buffered saline solution or such similar solution mixed with the oil in a 1:1 to 1:20 ratio and further preferably comprising a mannid mono-ester, e.g., mannid mono oleate or mannid mono acetate and a surface active agent such as one of the sorbitans, e.g., tween 40, 60 or 80, to form an emulsion.

According to the present invention there is also provided a method for vaccinating chicks and poults against Newcastle Disease, comprising administering to the respiratory tract of said chicks and poults, at any time immediately after hatching and thereafter, a live immunogenic lentogenic strain of Newcastle Disease virus (NDV) in combination with a liquid containing a mineral or vegetable oil adjuvant carrier, to produce local antibodies in the respiratory tract thereof and confer an extended immunity against Newcastle Disease for at least 30 days.

It has been found that in counterdistinction to prior methods wherein immunization of the mother hen resulted in maternal antibodies which interfered with establishment of active immunity in the chicks maternal antibodies do not, or insignificantly, interfere with the efficiency of the present method.

On the other hand the method of the present invention was found to be effective also with chicks from unimmunized hens in which maternal antibodies are not present and in any case the lack of maternal antibodies does not reduce the efficacy of the present method.

In a second aspect of the present invention there is now also provided a method for vaccinating chicks and poults, hatched from eggs of immunized hens, against Newcastle Disease, comprising administering to the respiratory tract of said chicks and poults, at any time immediately after hatching and thereafter, a live immunogenic mesogenic strain of Newcastle Disease virus (NDV) in combination with a liquid containing a mineral or vegetable oil adjuvant carrier, to produce local antibodies in the respiratory tract thereof and confer an extended immunity against Newcastle Disease.

It has been found that in counterdistinction to prior methods wherein immunization of the mother hen resulted in maternal antibodies which interferred with establishment of immunity in the chicks, in this present method, utilizing a live mesogenic strain of NDV, maternal antibodies do not prevent the appearance of local immunity.

Thus the present method enables the safe use of a mesogenic strain of NDV in very young chicks, which ordinarily may react unfavorably with harsh side effects.

Thus in this second method a continuity of immunity is established with the maternal immunity being supplemented and superimposed by the establishment of local immunity from the present vaccine.

As indicated hereinbefore, lentogenic strains were used in the past for the immunization of chicks by coarse spray, by aerosol, or by intraocular or intranasal drop methods, but always in aqueous solutions, and/or with simultaneous systemic injection of inactivated vaccine, given intramuscularly or subcutaneously.

As shown in comparative example B hereinafter, the overwhelming majority of chicks immunized at one day with aqueous solutions of lentogenic (La Sota) strains only, did not possess immunity after one month. In contradistinction, 97% of the chicks immunized with a live immunogenic lentogenic strain of NDV in combination with a liquid containing a mineral or vegetable oil adjuvant carrier according to the present invention survived challenge 51 days after immunization.

In the second aspect of the present invention, the presently proposed method makes it possible to use in chicks a live strain with elevated virulence, (mesogenic) and to establish a long-term immunity therewith, there being no adverse side effects in the immunized chicks.

Thus, according to the present invention, for the first time young chicks and preferably newly hatched chicks, i.e., chicks less than a week old can safely be immunized with mesogenic strains of ND, the term mesogenic as used herein including those strains normally categorized as mesogenic, as well as those strains which are intermediate between lentogenic and mesogenic and which due to their elevated virulence are not categorized as lentogenic.

The vaccine is applied intranasally and/or intraocularly. Although the best method to use is individual vaccination by applying a drop onto the eye and/or intranasally, vaccination by aerosol or by delivering a coarse spray of large droplets over the heads of said chicks and poults can also be used. Also, beak-dipping can successfully be used in the present method.

Both the lentogenic and mesogenic vaccines of the present invention are easy to prepare. They are feasible and their main advantage is that they confer immunity following but one application to one day old or older chicks.

This mode of vaccination using an appropriate live mesogenic strain in combination with a liquid containing a mineral or vegetable oil adjuvant carrier may be especially suitable for the distribution of immunized chicks to endemic areas. It also has the major economic advantage of enabling hatcheries to market already immunized chicks. Furthermore, veterinary authorities can easily supervise vaccination programs by inspecting hatcheries instead of the many farms to which chicks and poults are sent.

The present invention solves the problems of poultry vaccination by providing a new approach to vaccination using an adequate live mesogenic or lentogenic NDV strain.

With regard to the use of a mesogenic strain, this method renders it non-transmissible, allowing it to replicate well in the respiratory tract but limiting it to that environment by the immune state of the chicks, the offsprings of routinely immunized layers. By this method immune chicks develop local antibodies, which confer long term immunity while humoral antibodies are present only at a low level. The immune state of the chicks was evidenced in challenge experiments against a velogenic strain of ND (Table 2), as described hereinafter. Immunity in chicks can be established even on the day of hatching following a single dose of vaccination, and it lasts for a surprisingly long time The immune state is dependent on the build-up of local immunity in the respiratory system, due to the presence of local antibodies. Immunity is evident from challenge experiments, where survival rate in vaccinated birds is high (80–100%).

With regard to the use of the lentogenic strain according to the present invention, immunity in chicks can be established even on the day of hatching following a single dose of vaccination. The immune state is dependent on the build-up of local immunity in the respiratory system, due to the presence of local antibodies. Immunity is evident from challenge experiments, where survival rate in vaccinated birds is high (75–100%).

The present method, regardless of its strain, will be effective against infection in all countries concerned, as follows from the 1977 Atlanta decision that all ND strains are serologically identical.

The experiments described hereinafter were carried out with three representative mesogenic strains: The Komarov (Haifa) strain, the Roakin strain and a mesogenic strain designated hereinafter as $ER_3$ which was isolated from an infected chicken during an outbreak of ND on a poultry farm.

The $ER_3$ strain has a MDT (mean death time) of 64.5 hours. It forms plaque without additives.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

1) Preparation of ND Strains

A routine procedure for the cultivation of virus in the allantoic sac of embryonated chicken eggs was used. Seed virus was inoculated to 9-12-day embryonated eggs in volumes of 0.1-0.2 ml/egg. The infected allantoic fluid was harvested, clarified by centrifugation and stored at 4°-10° C. The antigen may be lyophilized and kept until used. Stock virus was kept in −70° or −20° C. Commercial lentogenic VH or Lasota strains can alternatively be purchased and used.

2) Vaccine Preparation

Before vaccination the ND live virus was diluted as predetermined in buffer, PBS pH 7.2-7.6 to contain between $10^5$-$10^7$ $EID_{50}$/dose. The antigen is mixed 1:5 with mineral oil and a volume of 0.05-0.1 ml is applied to a chick. Mineral oil or vegetable oil used is of USP quality, but many kinds of such oils are available and most of them will be suitable for this use.

3) Vaccination of Chicks with lentogenic strain

One-day or older commercial light breed or broiler type chicks were individually vaccinated intranasally (I.N.) and/or intraocularly (I.O.) with a volume of 0.05-0.1 ml to both nostrils. Aerosol or Coarse Spray or beak-dipping may also be used.

4) Challenge Experiments

Chicks were immunized at 1 day of age or at 4-5 days of age, as described above, by an intranasal or intraocular route.

Challenge by contact was carried out. Chickens infected with velogenic NDV were introduced in contact with the experimental groups.

Following one application, immunized chicks were isolated and challenged at different time intervals with a velogenic strain. Identical results were obtained with light and heavy breeds. Control non-immunized chicks that were kept together were challenged simultaneously. All controls died indicating that the vaccine was not transmitted to contacts when vaccinated by the present method, and that there was no boosting by any accidental contact with ND.

Comparative Example A

Three week old chicks, free of maternal antibodies, were immunized intranasally and intraocularly with the lentogenic VH strain of NDV with or without mineral oil. Twenty five days later the level of HI antibodies in the lungs was twice as high in the lungs of chicks immunized with the oil (1:56) as compared to 1:22 in those immunized without oil and 1:2 in the control unimmunized chicks.

It is believed that the extended period of protection is based on higher level of local secretory antibodies that are elicited in the lungs of the immunized chicks.

Comparative Example B

One day old chicks were immunized with aqueous solutions of lentogenic LaSota strain alone and with lentogenic strain mixed with mineral oil.

Ninety percent of the chicks immunized introcularly or by spray with the Lasota strain alone at one day died after challenge.

50 1-day old chicks were vaccinated with LaSota strain Newcastle disease virus mixed with oil. 20 chicks were left as unvaccinated controls. 30 vaccinated and 10 control birds were challenged with velogenic NDV at 51 days of age and 20 unvaccinated as well as 10 controls were challenged at 64 days of age. The results are summarized in Table 1:

TABLE 1

Survival of Chickens after Challenge Exposure

| Age of Challenge | No. Challenged Vaccinated | No. Challenged Controls | No. (%) Survival Vaccinated | No. (%) Survival Controls |
|---|---|---|---|---|
| 51 days | 30 | 10 | 29 (97%) | 0 (0%) |
| 64 days | 20 | 10 | 11 (55%) | 1 (10%) |

Vaccination of Chicks with mesogenic strains

One-day or older chicks from routinely immunized flocks were individually vaccinated intranasally (I.N.) and/or intraocularly (I.O.) with a volume of 0.05-0.1 ml to both nostrils. Aerosol or Coarse Spray or beak-dipping may also be used.

The vaccine strain was not transmitted to control non-immunized chicks that were located in the same cage, as evidenced by lack of seroconversion and death upon exposure in the challenge experiments (see Tables 2, 3).

A follow-up for adverse side effects in the chicks as a result of vaccination, as well as for antibody response (local and humoral) and resistance to challenge, were carried out. Adverse side effects, or death, were not recorded in the vaccinated chicks. In one experiment with the ER-3 strain, chickens were kept for several months and started laying in a normal manner, while a satisfactory level of local HI antibodies in the lungs was maintained for all those months (Table 2 hereinafter).

Titers of HI antibodies in the serum were low (1:4-1:32) as expected, since only a small amount of antigen leaked into the circulation, most of it remaining in the respiratory tract due to the protective maternal antibodies.

6) Challenge Experiments

Chicks were immunized at 1 day of age or at 4-5 days of age, as described above, by an intranasal, intraocular or aerosol route.

Challenge by contact was carried out. Chickens infected with velogenic NDV were introduced in contact with the experimental groups.

Following one application, immunized chicks were isolated and challenged at different time intervals with a velogenic strain. Heavy and light breed chicks were used, with identical results. Control non- immunized chicks that were kept together were challenged simultaneously. All controls died indicating that the vaccine strain was non-transmissible to contacts, that there was no boosting by any accidental contact with ND and that the velogenic NDV used was indeed deadly to susceptible chickens.

The high level of protection during several months is well demonstrated in Table 2 hereinafter. ER$_3$ strain conferred the longest immunity in vaccinated chicks but Roakin and Komarov strains also elicited an unexpectedly good and long-term immunity.

An additional parameter indicative of the protective local immune state was the lack of boosting effect, following exposure to the velogenic strain, used in challenge exposure. No elevation in serum HI antibody titers could be found after challenge, emphasizing that a barrier against subsequent virus infection is mounted in the respiratory tract due to the vaccination early in life.

TABLE 2

HI antibody titers in chicks immunized at one day with ER-3

| Group | | Reciprocal titers months post immunization | | | | | |
|---|---|---|---|---|---|---|---|
| | | 1 | 2 | 3 | 4 | 5 | 6½ |
| Vacci-nated | local | *32–64 | 32–64 | 32–64 | 32 | 32–64 | 32–64 |
| | humoral | 8–16 | 16–32 | 16 | 16–32 | 8 | 8–16 |
| Control | local | neg | n.d. | n.d. | n.d. | n.d. | neg |
| | humoral | 4 | <2 | n.d. | 2 | <4 | <4 |

*32–64 are the reciprocals of the highest dilutions of lung homogenate or serum inhibiting hemagglutination (HI titre).

TABLE 3

Survival of chickens after challenge exposure

| Treatment | No. of chickens | months after vaccination | No. of dead | Percentage* of survival |
|---|---|---|---|---|
| Vaccine ER$_3$ strain | 34 | 1 | 0 | 100.0 |
| | 27 | 3 | 4 | 85.2 |
| | 6 | 4 | 0 | 100.0 |
| | 13 | 5 | 2 | 84.6 |
| | 11 | 7 | 0 | 100.0 |
| | 10 | 10 | 0 | 100.0 |
| Roakin | 10 | 1½ | 0 | 100.0 |
| | 7 | 3 | 4 | 42.9 |
| Komarov | 10 | 1¾ | 1 | 90.0 |

Groups of control chicks (10–12 chicks in each group) non immunized were kept under the same roof with the immunized chicks and were challenge exposed at the same time. All control chickens died within 6–8 days.
*Chicks were observed for 3–4 weeks post challenge exposure.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A vaccine against Newcastle Disease comprising a live immunogenic lentogenic or mesogenic strain of Newcastle Disease virus in combination with a liquid containing a mineral or vegetable oil adjuvant carrier for the administering thereof to the respiratory tract of poults or chicks.

2. A vaccine against Newcastle Disease comprising a live immunogenic lentogenic strain of Newcastle Disease virus in combination with a liquid containing a mineral or vegetable oil adjuvant carrier for the administering thereof to the respiratory tract of poults or chicks.

3. A vaccine according to claim 2 wherein said liquid comprises an aqueous solution in combination with said mineral or vegetable oil.

4. A vaccine according to claim 2 further comprising a mannid mono-ester.

5. A vaccine according to claim 2 further comprising a sorbitan surface active agent.

6. A vaccine against Newcastle Disease comprising a live immunogenic mesogenic strain of Newcastle Disease virus in combination with a liquid containing a mineral or vegetable oil adjuvant carrier for the administering thereof to the respiratory tract of poults or chicks hatched from eggs of immunized hens.

7. A vaccine according to claim 6 wherein said liquid comprises an aqueous solution in combination with said mineral or vegetable oil.

8. A vaccine according to claim 6 further comprising a mannid mono-ester.

9. A method for vaccinating chicks and poults against Newcastle Disease, comprising administering to the respiratory tract of said chicks and poults a live lentogenic strain of Newcastle Disease virus (NDV) in combination with a liquid containing a mineral or vegetable oil adjuvant carrier, to produce local antibodies in the respiratory tract thereof and confer an extended immunity against Newcastle Disease.

10. A method for vaccinating poults and chicks after hatching and less than one week old according to claim 9 comprising administering said vaccine to said poults and chicks.

11. A method according to claim 9 comprising administering said vaccine to poults and chicks after hatching and up to six weeks of age.

12. A method as claimed in claim 9 comprising administering said live NDV strain intranasally.

13. A method as claimed in claim 9 comprising administering said live NDV strain intraocularly.

14. A method as claimed in claim 9 comprising administering said live NDV strain in the form of an aerosol.

15. A method as claimed in claim 9 comprising administering said live NDV strain by delivering a coarse spray of large droplets over the heads of said chicks and poults.

16. A method as claimed in claim 9 comprising administering said live NDV strain by dipping the beaks of chicks or poults into a live lentogenic strain of Newcastle Disease Virus in combination with a liquid containing mineral or vegetable oil adjuvant carrier.

17. A method for vaccinating chicks and poults, hatched from eggs of immunized hens, against Newcastle Disease, comprising administering to the respiratory tract of said chicks and poults a live immunogenic mesogenic strain of Newcastle Disease virus (NDV) in combination with a liquid containing a mineral or vegetable oil adjuvant carrier, to produce local antibodies in the respiratory tract thereof and confer an extended immunity against Newcastle Disease.

18. A method for vaccinating poults and chicks after hatching and less than one week old according to claim 17 comprising administering said vaccine to said poults and chicks.

19. A method according to claim 17 comprising administering said vaccine to poults and chicks after hatching and up to six weeks of age.

20. A method as claimed in claim 17 comprising administering said live NDV strain intranasally.

21. A method as claimed in claim 17 comprising administering said live NDV strain intraocularly.

22. A method as claimed in claim 17 comprising administering said live NDV strain by dipping of the beaks of chicks and poults into a mixture of vaccine and oil.

23. A method as claimed in claim 17 comprising administering said live NDV strain in the form of an aerosol.

24. A method as claimed in claim 17 comprising administering said live NDV strain by delivering a coarse spray of large droplets over the heads of said chicks and poults.

* * * * *